United States Patent [19]

Kühlmeyer et al.

[11] Patent Number: 5,342,823
[45] Date of Patent: Aug. 30, 1994

[54] SULFONYLUREAS

[75] Inventors: Rainer Kühlmeyer, Ihringen, Fed. Rep. of Germany; Werner Töpfl, Dornach; Werner Föry, Riehen, both of Switzerland

[73] Assignee: Ciba-Geigy Corporation, Ardsley, N.Y.

[21] Appl. No.: 18,603

[22] Filed: Feb. 17, 1993

[30] Foreign Application Priority Data

Feb. 20, 1992 [CH] Switzerland .................. 522/92-7

[51] Int. Cl.$^5$ ................ C07D 407/14; A01N 43/54
[52] U.S. Cl. .................... 504/215; 544/320; 544/321; 544/324; 544/331
[58] Field of Search ............... 504/215; 544/320, 321, 544/324, 331

[56] References Cited

U.S. PATENT DOCUMENTS

| | | | |
|---|---|---|---|
| 4,028,373 | 6/1977 | Hromatka | 260/301 |
| 4,090,020 | 5/1978 | Binder | 544/48 |
| 4,175,085 | 11/1979 | Binder | 549/65 |
| 4,579,584 | 4/1986 | Meyer | 71/93 |
| 4,701,535 | 10/1987 | Levitt | 549/60 |
| 4,741,760 | 5/1988 | Meyer | 71/92 |
| 4,892,946 | 1/1990 | Levitt | 544/321 |

FOREIGN PATENT DOCUMENTS

| | | |
|---|---|---|
| 1243674 | 10/1988 | Canada . |
| 0007687 | 2/1980 | European Pat. Off. . |
| 0030138 | 6/1981 | European Pat. Off. . |
| 0073562 | 3/1983 | European Pat. Off. . |

*Primary Examiner*—John M. Ford
*Attorney, Agent, or Firm*—Kevin T. Mansfield

[57] ABSTRACT

N-Arylsulfonyl-N'-pyrimidinyl-and N'-triazinylureas of formula I

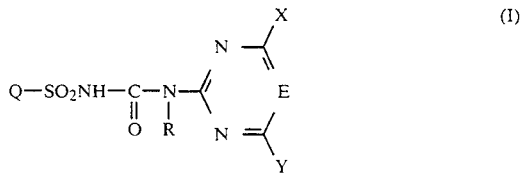

wherein Q is

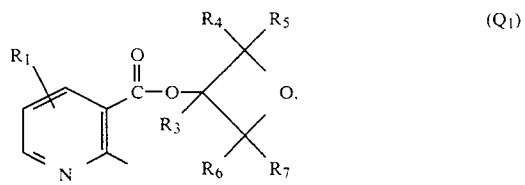

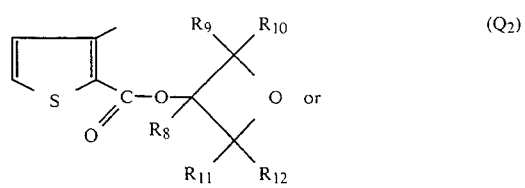

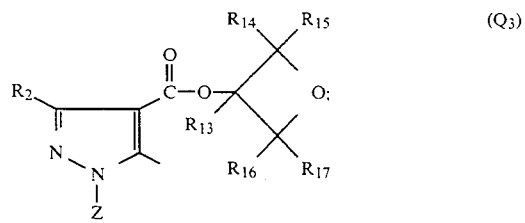

R is hydrogen or methyl;
$R_1$ is hydrogen, fluoro, chloro, $C_1$–$C_4$alkyl or methoxy;
$R_2$ is hydrogen, fluoro or chloro;
$R_3$, $R_4$, $R_5$, $R_6$ and $R_7$ are each independently of one another hydrogen or $C_1$–$C_4$alkyl;
$R_8$, $R_9$, $R_{10}$, $R_{11}$ and $R_{12}$ are each independently of one another hydrogen or $C_1$–$C_4$alkyl;
$R_{13}$, $R_{14}$, $R_{15}$, $R_{16}$ and $R_{17}$ are each independently of one another hydrogen or $C_1$–$C_4$alkyl;

(Abstract continued on next page.)

Z is methyl or 2-pyridyl;
E is methine or nitrogen;
X is $C_1$–$C_4$alkyl, $C_1$–$C_4$alkoxy, $C_1$–$C_4$haloalkoxy, $C_1$–$C_4$haloalkylthio, $C_1$–$C_4$alkylthio, $C_2$–$C_5$alkoxyalkyl, $C_2$–$C_5$alkoxyalkoxy, $C_2$–$C_5$alkylthioalkyl or cyclopropyl;
Y is $C_1$–$C_4$alkyl, $C_1$–$C_4$alkoxy, $C_1$–$C_4$haloalkoxy, $C_1$–$C_4$haloalkyl, $C_1$–$C_4$haloalkylthio, $C_1$–$C_4$alkylthio, halogen, $C_2$–$C_5$alkoxyalkyl, $C_2$–$C_5$alkoxyalkoxy, amino, $C_1$–$C_3$alkylamino or di-($C_1$–$C_3$alkyl)amino;

and the salts of these compounds with amines, alkali metal or alkaline earth metal bases or with quaternary ammonium bases, have good pre-and postemergence selective herbicidal and growth regulating properties.

19 Claims, No Drawings

SULFONYLUREAS

The present invention relates to novel N-arylsulfonyl-N'-pyrimidinyl- and -N'-triazinylureas having herbicidal and plant growth regulating properties, to their preparation, to composition containing them and to the use thereof for controlling weeds, preferably selectively, in crops of useful plants or for regulating and inhibiting plant growth.

Herbicidally active ureas, triazines and pyrimidines are commonly known in the art. Such compounds are disclosed, inter alia, in European patent applications 0 007 687, 0 030 138, 0 073 562, 0 126 711 and in U.S. Pat. No. 4,701,535.

Novel sulfonylureas having herbicidal and plant growth regulating properties have now been found.

The novel N-arylsulfonyl-N'-pyrimidinyl- and N'-triazinylureas have the formula I

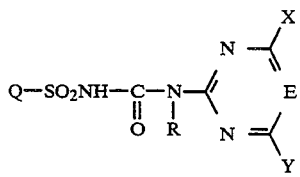
(I)

wherein
Q is

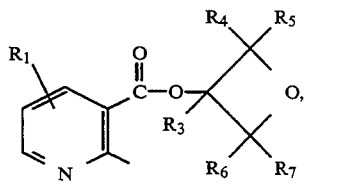 (Q$_1$)

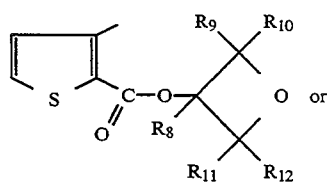 (Q$_2$) or

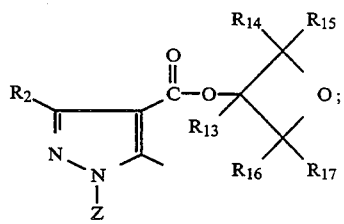 (Q$_3$);

R is hydrogen or methyl;
R$_1$ is hydrogen, fluoro, chloro, C$_1$–C$_4$alkyl or methoxy;
R$_2$ is hydrogen, fluoro or chloro;
R$_3$, R$_4$, R$_5$, R$_6$ and R$_7$ are each independently of one another hydrogen or C$_1$–C$_4$alkyl;
R$_8$, R$_9$, R$_{10}$, R$_{11}$ and R$_{12}$ are each independently of one another hydrogen or C$_1$–C$_4$alkyl;
R$_{13}$, R$_{14}$, R$_{15}$, R$_{16}$ and R$_{17}$ are each independently of one another hydrogen or C$_1$–C$_4$alkyl;
Z is methyl or 2-pyridyl;
E is methine or nitrogen;
X is C$_1$–C$_4$alkyl, C$_1$–C$_4$alkoxy, C$_1$–C$_4$haloalkoxy, C$_1$–C$_4$haloalkylthio, C$_1$–C$_4$alkylthio, C$_2$–C$_5$alkoxyalkyl, C$_2$–C$_5$alkoxyalkoxy, C$_2$–C$_5$alkylthioalkyl or cyclopropyl;
Y is C$_1$–C$_4$alkyl, C$_1$–C$_4$alkoxy, C$_1$–C$_4$haloalkoxy, C$_1$–C$_4$haloalkyl, C$_1$–C$_4$haloalkylthio, C$_1$–C$_4$alkylthio, halogen, C$_2$–C$_5$alkoxyalkyl, C$_2$–C$_5$alkoxyalkoxy, amino, C$_1$–C$_3$alkylamino or di-(C$_1$–C$_3$alkyl)amino;
and the salts of these compounds.

Y as halogen may suitably be: fluoro, chloro, bromo and iodo, fluoro, chloro and bromo.

R$_1$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, X and Y as C$_1$–C$_4$alkyl are typically: methyl, ethyl, n-propyl, isopropyl, n-butyl, sec-butyl, isobutyl or tert-butyl. The alkyl groups preferably contain 1 to 3 carbon atoms.

Y as C$_1$–C$_4$haloalkyl is preferably fluoro-, chloro-, bromo- or iodo-substituted alkyl. Among these, preferred substituents are alkyl groups which are substituted by 1 to 3 halogen atoms, preferably by fluoro or chloro, and are typically fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl. Difluoromethyl and trifluoromethyl are preferred.

X and Y as C$_1$–C$_4$alkoxy are typically methoxy, ethoxy, propoxy, isopropoxy, n-butoxy, isobutoxy, sec-butoxy and tert-butoxy. Methoxy and ethoxy are preferred.

X and Y as C$_1$–C$_4$haloalkoxy are typically difluoromethoxy, trifluoromethoxy, 2,2,2-trifluoroethoxy, 1,1,2,2-tetrafluorethoxy, 2-fluoroethoxy, 2-chloroethoxy and 2,2-difluoroethoxy. Difluoromethoxy and trifluoromethoxy are preferred.

X and Y as C$_2$–C$_5$alkoxyalkyl are typically methoxymethyl, methoxyethyl, ethoxymethyl, ethoxyethyl as well as propoxymethyl.

X and Y as C$_1$–C$_4$alkylthio are typically: methylthio, ethylthio, propylthio, isopropylthio, n-butylthio, isobutylthio, sec-butylthio or tert-butylthio. Methylthio and ethylthio are preferred.

X and Y as C$_1$–C$_4$haloalkylthio are preferably fluoro-, chloro-, bromo- or iodo-substituted alkylthio. Among these, preferred substituents are alkylthio groups which are substituted by 1 to 3 halogen atoms, preferably by fluoro or chloro, and are typically fluoromethylthio, difluoromethylthio, trifluoromethylthio, chloromethylthio, dichloromethylthio, trichloromethylthio.

X as C$_2$–C$_5$alkylthioalkyl is suitably methylthioethyl, ethylthioethyl, propylthioethyl, isopropylthiomethyl, preferably methylthiomethyl and ethylthioethyl.

X and Y as C$_2$–C$_5$alkoxyalkoxy are suitably methoxymethoxy, methoxyethoxy, methoxypropoxy, ethoxymethoxy, ethoxyethoxy as well as propoxymethoxy.

Y as C$_1$–C$_3$alkylamino is typically methylamino, ethylamino, n-propylamino or isopropylamino. Y as di(C$_1$–C$_3$alkyl)amino as typically dimethylamino, methylethylamino, diethylamino or n-propylmethylamino.

The invention also embraces the salts which the compounds of formula I are able to form with amines, alkali metal and alkaline earth metal bases or quaternary ammonium bases.

Preferred alkali metal and alkaline earth metal hydroxides suitable as salt formers include hydroxides of lithium, sodium, potassium, magnesium or calcium, most preferably the hydroxides of sodium or potassium.

Representative examples of amines suitable for salt formation are: primary, secondary and tertiary aliphatic and aromatic amines such as methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, m ethyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethylethanolamine, N-ethylpropanolamine, N-butylethanolamine, allylamine, n-butenyl-2-amine, n-penten-2-yl-amine, 2,3-dimethylbuten-2-ylamine, dibuten-2-ylamine, n-hexen-2-ylamine, propylenediamine, diethanolamine, trimethylamine, triethylamine, tri-n-propylamine, tri-iso-propylamine, tri-n-butylamine, triisobutylamine, tri-sec-butylamine, tri-n-amylamine; heterocyclic amines such as pyridine, quinoline, isoquinoline, morpholine, piperidine, pyrrolidine, indoline, quinuclidine and azepine; primary arylamines such as anilines, methoxyanilines, ethoxyanilines, o-, m- and p-toluidine, phenylenediamines, benzidines, naphthylamines and o-, m- and p-chloroaniline; and preferably ethylamine, propylamine, diethylamine or triethylamine, and, most preferably, isopropylamine and diethanolamine.

Illustrative examples of quaternary ammonium bases are in general the cations of haloammonium salts, conveniently the tetramethylammonium cation, the trimethylbenzylammonium cation, the triethylbenzylammonium cation, the tetraethylammonium cation, the trimethylethylammonium cation, and also the ammonium cation.

Among the compounds of formula I, those compounds are preferred in which R is hydrogen, and preferably E is methine or nitrogen. Within the scope of these preferences, Q is preferably $Q_1$, wherein $R_1$ is preferably hydrogen, or $Q_3$, wherein $R_2$ is preferably hydrogen or chloro.

Compounds of formula I that also merit particular interest are the group of compounds of formula I, wherein Q is $Q_2$, X is $C_1$-$C_3$alkyl, $C_1$-$C_3$alkoxy, $C_1$-$C_2$-haloalkoxy or cyclopropyl; and Y is $C_1$-$C_3$alkyl, $C_1$-$C_3$alkoxy, $C_1$-$C_2$haloalkoxy, trifluoromethyl, difluoromethyl, fluoromethyl, methoxymethyl, fluoro, chloro, amino, methylamino, dimethylamino, or methylthio, and E is methine or nitrogen, and R is preferably hydrogen.

Preferred compounds of formula I are also those wherein

Q is $Q_1$ and $R_3$, $R_4$, $R_5$, $R_6$ and $R_7$ are hydrogen; or
Q is $Q_2$ and $R_8$, $R_9$, $R_{10}$, $R_{11}$ and $R_{12}$ are hydrogen; or
Q is $Q_3$ and $R_{13}$, $R_{14}$, $R_{15}$, $R_{16}$ and $R_{17}$ are hydrogen.

In particularly preferred compounds of formula I, X is $C_1$-$C_3$alkyl, $C_1$-$C_3$alkoxy, $C_1$-$C_2$haloalkoxy or cyclopropyl, preferably methyl, methoxy, difluoromethoxy, ethoxy or cyclopropyl; and Y is $C_1$-$C_3$alkyl, $C_1$-$C_3$alkoxy, $C_1$-$C_2$haloalkoxy, trifluoromethyl, difluoromethyl, fluoromethyl, methoxymethyl, fluoro, chloro, amino, methylamino, dimethylamino, methylthio, but is preferably methyl, ethyl, methoxy, difluoromethoxy, ethoxy, 2,2,2-trifluoroethoxy, chloro, methylamino, dimethylamino or methoxymethyl.

A particularly preferred individual compound falling within the scope of formula I is N-[(3-oxetan-3-oxycarbonyl)pyridin-2-ylsulfonyl]-N'-(4,6-dimethoxypyrimidin-2-yl)urea.

The compounds of formula I can be prepared either by a) reacting a sulfonamide of formula IIa, IIb or IIc

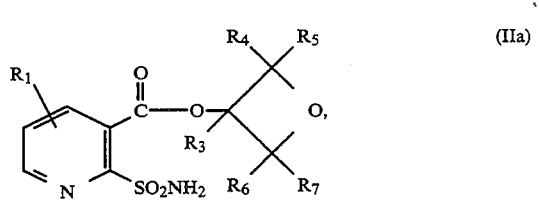

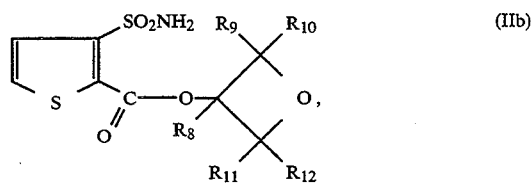

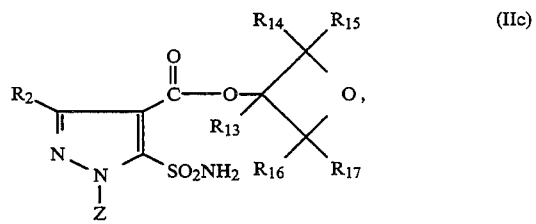

wherein the substituents are each as defined for formula I, in the presence of a base, with a pyrimidinyl carbamate or triazinyl carbamate of formula III

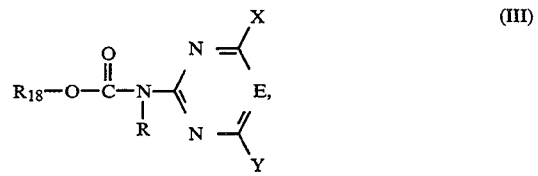

wherein R, X and Y are as defined for formula I and $R_{18}$ is phenyl or $C_1$-$C_4$alkyl- or halogen-substituted phenyl, or b) reacting a sulfonyl carbamate of formula IVa, IVb or IVc

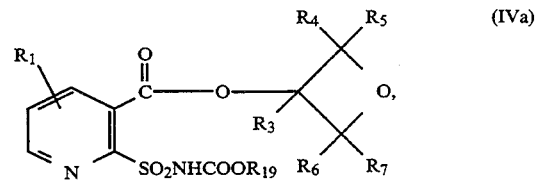

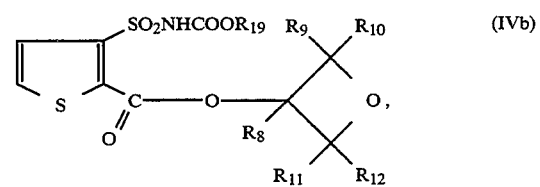

-continued

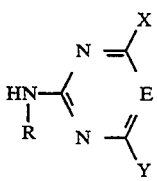 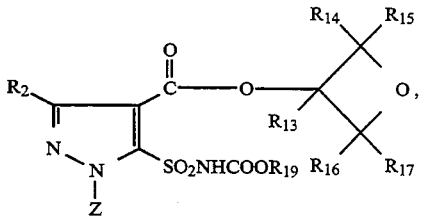   (IVc)

wherein the substituents are each as defined for formula I, and $R_{19}$ is phenyl or $C_1$–$C_4$alkyl- or halogen-substituted phenyl, in the presence of a base, with an amine of formula V

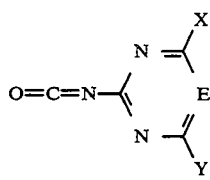   (V)

wherein R, E, X and Y are as defined for formula I, or c) reacting a sulfonamide of formula IIa, IIb or IIc

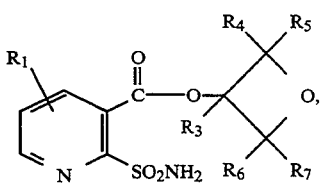   (IIa)

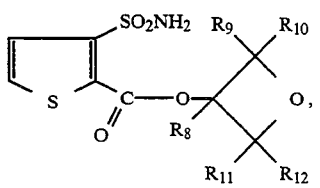   (IIb)

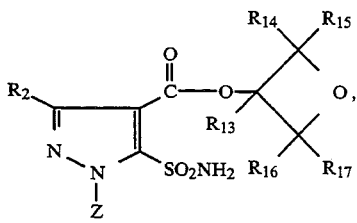   (IIc)

wherein the substituents are each as defined for formula I, in the presence of a base, with a pyrimidinyl isocyanate or triazinyl isocyanate of formel VI $$O=C=N-\underset{\substack{\\}}{\begin{array}{c}X\\E\\Y\end{array}}$$   (VI)

wherein E, X and Y are as defined for formula I.

Compounds of formula I can also be prepared by reacting a compound of formula VIIa, VIIb or VIIc

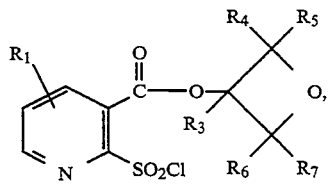   (VIIa)

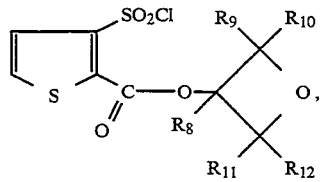   (VIIb)

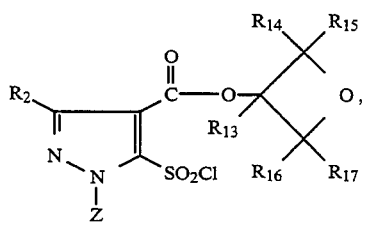   (VIIc)

wherein the substituents are each as defined for formula I, with an amine of formula V, in the presence of an ammonium, phosphonium, sulfonium or alkali metal cyanate salt of formula VIII $$M^+OCN^-  \quad (VIII)$$

wherein M is an alkali metal or the group $R_{20} R_{21} R_{22} R_{23}Q$, wherein $R_{20}$, $R_{21}$, $R_{22}$ and $R_{23}$ are each independently of one another $C_1$–$C_{18}$alkyl, benzyl or phenyl, and the total number of carbon atoms is not greater than 36; and Q is nitrogen, sulfur or phosphorus. Such reactions are disclosed in Swiss patent 662 348.

The reactions to give the compounds of formula I are conveniently carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane; nitriles such as acetonitrile or propionitrile, amides such as dimethyl formamide, diethyl formamide or N-methylpyrrolidinone. The reaction temperatures are preferably in the range from −20° to +120° C.

The reactions are normally slightly exothermic and can be carried out at room temperature. To shorten the reaction time or also to initiate the reaction, it is advantageous to apply heat for a brief time up to the boiling point of the reaction mixture. The reaction times can also be shortened by addition of a few drops of a base as reaction cataylst. Particularly suitable bases are tertiary amines such as trimethylamine, triethylamine, quinuclidine, 1,4-diazabicyclo(2.2.2)octane, 1,5-diazabicyclo(4.3.0)non-5-ene or 1,5-diazabicyclo(5.4.0)undec-7-ene. It is also possible to use inorganic bases such as hydrides, typically sodium or calcium hydride, hydroxides such as sodium and potassium hydroxide, carbonates such as sodium and potassium carbonate, or hydrogen carbonates such as potassium and sodium hydrogen carbonate.

The final products of formula I can be isolated by concentration and/or evaporation of the solvent and purified by recrystallising or triturating the solid residue in solvents in which they are not readily soluble, typically in ethers, aromatic hydrocarbons or chlorinated hydrocarbons.

In the above described processes for the preparation of compounds of formula I, $R_{18}$ and $R_{19}$ are preferably phenyl which may be substituted by $C_1$-$C_4$alkyl or halogen, and are most preferably unsubstituted phenyl.

The sulfonamides of fomulae IIa, IIb and IIc are novel compounds which have been specially developed and prepared for the synthesis of the compounds of formula I. They can be obtained from the corresponding sulfochlorides of formula VIIa, VIIb and VIIc by reaction with ammonia. Such reactions are known and familiar to the those skilled in the art.

The sulfochlorides of formula VIIa, VIIb and VIIc are prepared by reacting the suitably substituted 2-chlorosulfonyl acid chlorides (q.v. e.g. D. Davis, Soc. 2042, 2044 (1932)) in the presence of a base, with a compound of formula IXa, IXb or IXc

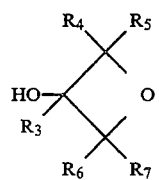  (IXa)

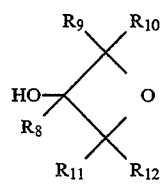  (IXb)

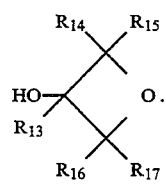  (IXc)

Such reactions are known and familar to those skilled in the art.

Phenylsulfochlorides of formulae VIIa and VIIc can also be obtained by reacting a ccompound of formula Xa or Xc

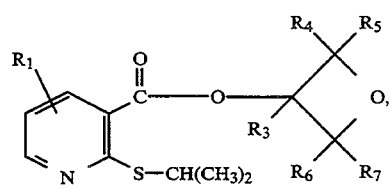  (Xa)

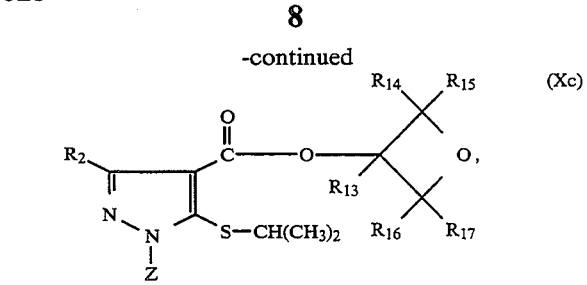  (Xc)

wherein the substituents are each as defined for formula I (q.v. e.g. H. Gilman, F. J. Webb, Am. Soc 71, 4062–4063), with thionyl chloride to give the corresponding aryl acid chloride, which is then converted with the appropriate compound of formula IXa or IXc, in the presence of a base, to the corresponding 2-isopropylthioaryl acid oxetan-3-yl ester in order, finally, by reaction with chlorine, to obtain the sulfochlorides of formulae VIIa and VIIc. Such reactions are known and familiar to those skilled in the art.

Compounds of formula VIIb can be prepared by the following process disclosed in DE-OS 2 534 689 and 2 706 859:

Scheme 1:

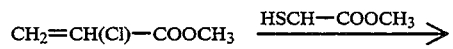

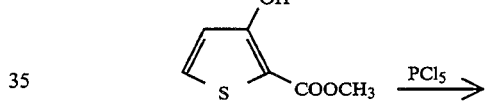

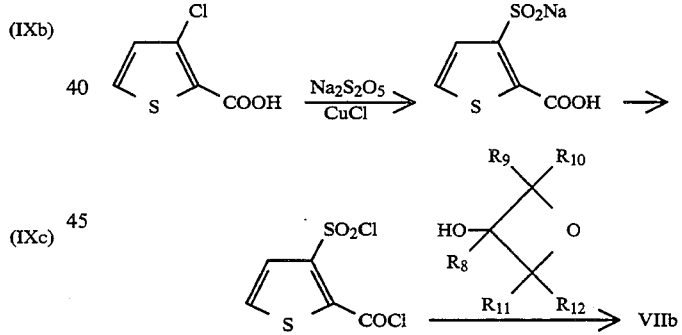

Compounds of formulae IXa, IXb and IXc are known or can be prepared by methods analogous to known ones (q.v. e.g. B. Lamm et al., Acta Chem. Scand. 28, 701 (1974) or J. Org. Chem. 48, 2953–2956 (1983)).

The sulfonyl carbamates of formulae IVa, IVb and IVc may conveniently be obtained by reacting the sulfonamides of formulae IIa, IIb and IIc with diphenyl carbamate in the presence of a base. Such reactions are known and familiar to those skilled in the art.

The amines of formula V are disclosed in European patent applications 0 007 687, 0 030 138, 0 073 562 and 0 126 711 and in U.S. Pat. No. 4,579,584.

Processes for the preparation of N-pyrimidinylcarbamates and N-triazinylcarbamates are disclosed, inter alia, in EP-A-0 101 670.

The compounds of formula I are normally used with success in rates of application of 0.001 to 2 kg/ha, preferably 0.005 to 1 kg/ha. The concentration necessary for the desired effect can be ascertained by experimentation. It will depend on the type of action, the development stage of the cultivated plant and of the weed, as well as as on the application (locus, time, method) and, in the light of these parameters, can vary over a wide range.

The compounds of formula I have good growth inhibiting and herbicidal properties which make them pre-eminently suitable for use in crops of useful plants, especially in crops of cereals, cotton, soybeans, rape, maize and rice. In addition to their good herbicidal action, the compounds of formula I are also readily biodegradable.

The invention also relates to herbicidal and plant growth regulating compositions which contain a novel compound of formula I, as well as to methods of inhibiting plant growth.

Plant growth regulators are substances which induce in or on the plant agronomically desirable biochemical and/or physiological and/or morphological changes.

The active ingredients present in the novel compositions influence plant growth in different manner in accordance with the time of application, concentration, type of application and environmental conditions. Plant growth regulators of formula I are able, inter alia, to inhibit the vegetative growth of plants. This kind of action is of interest for area of grass, ornamentals, fruit plantations, road embankments, sports grounds and industrial parks, and also for the selective inhibition of side-shoots, as in tobacco plants. In crop growing, the inhibition of vegetative growth in cereals results in reduced lodging by strengthening the stalks. Similar agronomic effects are obtained in rape, sunflowers, maize and other crop plants. In addition, inhibition of vegetative growth permits the number of plants per unit area to be increased. A further utility of growth regulators is the selective control of cover plants in plantations or crops with wide row spacing by strong growth inhibition without destroying said cover plants, so that these latter cannot compete with the principal crop and the positive effects, such as prevention of erosion, nitrogen fixation and soil loosening, are retained.

By a method of inhibiting plant growth is meant the control of natural plant development without any change in the life cycle of the plant which is determined by genetic characteristics to cause a mutation. The method of growth regulation is applied at a development time of the plant which shall be determined in the individual case. Application of the compounds of formula I can be made pre- or postemergence, typically to the seeds or seedlings, roots, tubers, stems, leaves, blossoms or other parts of the plants. This can be done by applying the compound of formula I itself or in the form of a composition to the plants and/or by treating the nutrient medium of the plant (soil).

Different methods and techniques may suitably be used for applying the compounds of formula I or compositions containing them for regulating plant growth, typically the following:

i) Seed dressing a) Dressing the seeds with a wettable powder formulation of the compound of formula I in a vessel to give a homogeneous distribution on the surface of the seeds (dry treatment), using up to 4 g of compound of formula I (when using a 50% formulation: up to 8.0 g of wettable powder) per 1 kg of seeds.

b) Dressing seeds with an emulsifiable concentrate of the compound of formula I or with an aqueous solution of a wettable powder formulation of the compound of formula I by method a) (wet treatment).

c) Dressing by immersing the seeds in a mixture containing up to 1000 ppm of compound of formula I for 1 to 72 hours and, if desired, subsequently drying the seeds (seed soaking).

Dressing the seeds or treatment of the emergent seedling are normally the preferred methods of application, because the treatment is directed entirely to the target crop. Normally 0.001 g to 4.0 g of active ingredient is used per 1 kg of seeds. Departures from the indicated limit concentrations to higher or lower levels are possible depending on the method employed, which also permits the use of other active ingredients or micronutrients (repeat dressings).

ii) Controlled release of active ingredient

A solution of the active ingredient is applied to mineral granulate substrates or polymerised granulates (urea/formaldehyde) and allowed to dry. If desired, a coating can be applied (coated granulates) which permits the growth regulator to be released over a specific period of time.

The compounds of formula I are used in unmodified form, as from the synthesis or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons such as cyclohexane or tetrahydronaphthalene, alcohols such as ethanol, propanol or butanol; glycols and their ethers and esters such as propylene glycol or dipropylene glycol ethers; ketones such as cyclohexanone, isophorone or diacetone alcohol; strongly polar solvents such as N-methyl-2-pyrrolidone, dimethyl sulfoxide or water; vegetable oils and their esters, e.g. rape oil, castor oil or soybean oil; and optionally silicone oils.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$-alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphated adduct of p-nonylphenol with 4 to 14 mol of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, caster oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I-III, Chemical Publishing Co., New York, 1980-1981.

Dr. Helmut Stache "Tensid-Taschenbuch" (Handbook of Surfactants), Carl Hanser Verlag, Munich/vienna 1981.

The compositions usually contain 0.1 to 99%, preferably 0.1 to 95%, of a compound of formula I, 1 to 99.9% of a solid or liquid adjuvant, and 0 to 25%, preferably 0.1 to 25%, of a surfactant.

Whereas commercial products will preferably be formulated as concentrates, the end user will normally use dilute formulations.

The compositions may also contain further ingredients such as stabilisers, e.g. epoxidised vegetable oils (epoxidised coconut oil, rapeseed oil or soybean oil), antifoams, we.g. silicone oil, preservatives, viscosity regulators, binders, tackifiers as well as fertilisers or other chemical agents to obtain special effects.

Preferred formulations are composed in particular of the following constituents (%=percentage by weight):

Emulsifiable concentrates compound of formula I: 1 to 20%, preferably 5 to 10%
surfactant: 5 to 30%, preferably 10 to 20%
liquid carrier: 50 to 94%, preferably 70 to 85%

Dusts compound of formula I: 0.1 to 10%, preferably 0.1 to 1%
solid carrier: 99.9 to 90%, preferably 99.9 to 99%

Suspension concentrates compound of formula I: 5 to 75%, preferably 10 to 50%
water: 94 to 25%, preferably 88 to 30%
surfactant: 1 to 40%, preferably 2 to 30%

Wettable powders compound of formula I: 0.5 to 90%, preferably 1 to 80%
surfactant: 0.5 to 20%, preferably 1 to 15%
solid carrier: 5 to 95%, preferably 15 to 90%

Granulates compound of formula I: 0.5 to 30%, preferably 3 to 15%
solid carrier: 99.5 to 70%, preferably 97 to 85%.

Preparation of the compounds of formula I

EXAMPLE 1

Preparation of 2-isopropylthionicotinic acid

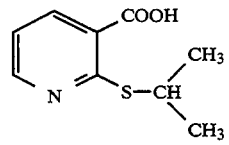

33.8 ml of 2-bromopropane are added dropwise to a mixture of 50.3 g of 2-mercaptonicotinic acid and 123 ml of a 5.3 molar methanolic solution of NaOCH$_3$ in 320 ml of methanol and the reaction mixture is heated under reflux. After 24 hours, the suspension is evaporated to dryness, and to the residue are added 250 ml of ethyl acetate and 175 ml of a 4N solution of NH₄Cl at a temperature of 10° C. Then the pH is adjusted to 8 with 80 g of KHCO₃. The aqueous phase is separated and washed with 200 ml of ethyl acetate. The organic phase is extracted with 2×50 ml of a saturated solution of KHCO₃, 50 ml of glacial acetic acid are added to the combined aqueous phase and the crystalline precipitate is isolated by filtration and dried. Recrystallisation from ethyl acetate/hexane 2:1 gives 47.1 g of 2-isopropylthionicotinic acid in the form of colourless crystals with a melting point of 164°–166° C.

EXAMPLE 2

Oxetan-3-yl 2-isopropylthionicotinate

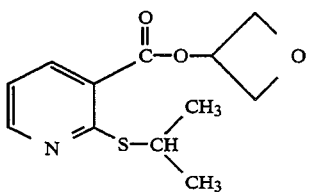

A mixture of 19.7 g of 2-isopropylthionicotinic acid prepared according to Example 1 and 22 ml of thionyl chloride in 100 ml of absolute toluene is stirred for 3 hours at 80° C. When evolution of gas has ceased, the reaction mixture is filtered and the mother liquor is concentrated to dryness under vacuum. The residual crude product (20.8 g of 2-isopropylthionicotinyl chloride as a yellow oil) is dissolved in 70 ml of absolute toluene and treated slowly at a temperature of 20°–25° C. with a mixture of 8.8 g of oxetan-3-ol and 8.5 ml pyridine dissolved in 20 ml of toluene. After stirring for 12 hours at a temperature of 20°–25° C., 100 ml of ice-water and 200 ml of diethyl ether are added, the organic phase is separated, and the aqueous phase is extracted with 2×100 ml of diethyl ether. The combined organic phase is dried and concentrated to give 27.4 g of oxetan-3-yl 2-isopropylthionicotinate in the form of a pale yellow oil. Purification by distillation at a bath temperature of 145°–150° C., 4×10⁻² bar) gives 19.7 g of an oil.

EXAMPLE 3

Preparation of 3-(oxetan-3-oxycarbonyl)pyridin-2-yl sulfochloride

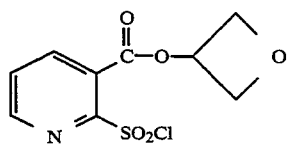

12.9 g of oxetan-3-yl 2-isopropylthionicotinate are suspended in 50 ml of water and 50 ml of glacial acetic acid. To the suspension are added 12.49 g of sodium acetate and, with efficient stirring, 10.9 g of chlorine are introduced at a temperature of −15° to −20° C. The resultant clear solution is warmed for 1 hour to room temperature and 300 ml of methylene chloride and 200 ml of ice-water are added. After phase separation and extraction of the aqueous phase with 100 ml of CH₂Cl₂, the combined organic phase is dried over MgSO₄, concentrated under vacuum and dried under a high vacuum (30° C./2×10² bar). The resultant 3-(oxetan-3-oxycarbonyl)pyridin-2-yl sulfochloride in the form of a yellow oil (8.9 g) is reacted direct to 3-(oxetan-3-oxycarbonyl)-pyridin-2-yl sulfonamide (q.v. Example P4).

EXAMPLE 4

Preparation of 3-(oxetan-3-oxycarbonyl)pyridin-2-ylsulfonamide (compound 4.001)

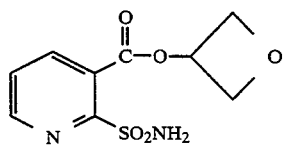

(4.001)

8.9 g of 3-(oxetan-3-oxycarbonyl)pyridin-2-yl sulfochloride are dissolved in 150 ml of absolute CH₂Cl₂ and the solution is cooled to c.−60° C. With efficient stirring, 1.8 g of NH₃ are introduced, and the reaction mixture is warmed slowly to room temperature. After stirring for 1 hour at room temperature, the suspension is concentrated under vacuum and 300 ml of ethyl acetate are added to the residue. The precipitate is removed by filtration and the mother liquor is concentrated under vacuum, giving 11.8 g of crude crystalline product. Purification under vacuum on silica gel (700 g of silica gel, eluant: hexane/ethyl acetate 1:1) gives 6.05 g of 3-(oxetan-3-oxycarbonyl)pyridin-2-yl sulfonamide (compound 4.001) in the form of white crystals with a melting point of 140°–142° C.

EXAMPLE 5

Preparation of 2-(oxetan-3-oxycarbonyl)thiophen-3-yl sulfochloride

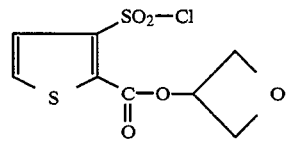

A mixture of 5.2 g of oxetanol and 5 ml of pyridine in 30 ml of absolute toluene is slowly added dropwise to 14.5 g of 3-chlorosulfonylthiophen-2-ylcarbonyl chloride in 150 ml of absolute toluene at a temperature of 0° to 5° C. After stirring for 3 hours at a temperature of 0° C., the reaction mixture is warmed to room temperature, stirred for a further hour, and then 100 ml of ether and 100 ml of ice-water are added. After phase separation, the aqueous phase is extracted with 100 ml of diethyl ether, the combined organic phase is washed with 50 ml of ice-water and 50 ml of brine, dried over Na₂SO₄ and concentrated to dryness under vacuum. The residual oil is recrystallised from a mixture of 25 ml of ethyl acetate and 25 ml of ether, to give 8.7 g of 2-(oxetan-3-oxycarbonyl)thiophen-3-yl sulfochloride in the form of beige crystals with a melting point of 92°–94° C.

EXAMPLE 6

Preparation of 2-(oxetan-3-oxycarbonyl)thiophen-3-yl sulfonamide (compound 5.001)

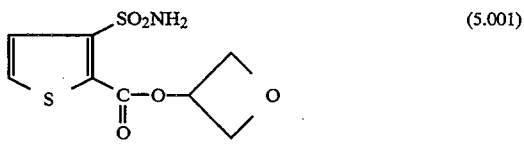
(5.001)

5.9 g of 2-(oxetan-3-oxycarbonyl)thiophen-3-yl sulfochloride are dissolved in 100 ml of methylene chloride and the solution is cooled to c. −60° C. With efficient stirring, 1.8 g of ammonia are introduced and the reaction mixture is slowly warmed to room temperature. After stirring for 1 hour at room temperature, the suspension is concentrated under vacuum and the residue is diluted with 30 ml of water, stirred for 30 minutes at room temperature, filtered, and the crude crystalline product is stirred in 10 ml of methanol and subsequently filtered. Yield: 4.6 g of 2-(oxetan-3-oxycarbonyl)thiophen-3-yl sulfonamide (compound 5.001) in the form of beige crystals with a melting point of 158°–160° C.

EXAMPLE 7

Preparation of 3-chloro-4-(methoxycarbonyl)-1-methyl-5-isopropylthiopyrazole

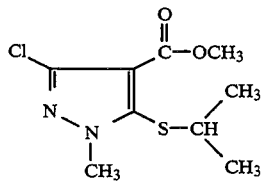

30 g of methyl 3,5-dichloro-1-methylpyrazol-4-ylcarboxylate and 25.5 g of potassium carbonate are suspended in 150 ml of DMSO and to this suspension are slowly added 16.1 ml of isopropylmercaptan at a temperature of 25° to 35° C. After stirring for 3 hours at room temperature, the reaction mixture is poured into 200 ml of ice-water and then 300 ml of ethyl acetate are added. After phase separation, the organic phase is washed with 100 ml of water and 100 ml of a saturated aqueous solution of sodium chloride, dried over MgSO$_4$ and concentrated to dryness under vacuum. Distillation of the residue (113°–114° C., 2×10$^{-3}$ bar) gives 31.5 g of 3-chloro-4-(methoxycarbonyl)-1-methyl-5-isopropylthiopyrazole in the form of a pale yellow oil.

EXAMPLE 8

Preparation of 3-chloro-4-(oxetan-3-oxycarbonyl)-1-methyl-5-isopropylthiopyrazole

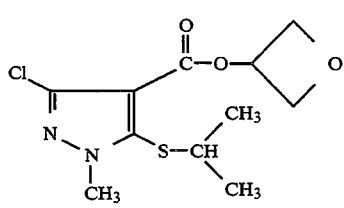

30.1 g of 3-chloro-4-(methoxycarbonyl)-1-methyl-5-isopropylthiopyrazole are suspended in 181 ml of 2N NaOH and the suspension is stirred at room temperature until a clear solution has formed. The solution is then cooled to 10°–15° C. and adjusted with 2N HCl to pH 2. After filtration and washing with water, 27.4 g of crude crystalline product are suspended in 150 ml of toluene and 35 g of thionyl chloride are slowly added at a temperature of 40°–50° C. When this addition is complete, the reaction mixture is stirred at a temperature of 80° C. until evolution of gas has ceased and cooled to room temperature.

The pale yellow solution is concentrated to dryness under vacuum and the residual oil (30.02 g) is taken up in 100 ml of toluene. A mixture of 16.83 g of oxetanol and 11.7 g of pyridine in 100 ml of toluene is slowly added dropwise at room temperature to this solution. After stirring for 10 hours at room temperature, the reaction mixture is poured into 250 ml of ice-water. The phases are separated and extracted with 2×100 ml of ethyl acetate. The combined organic phase is washed with 100 ml of water and 100 ml of a saturated aqueous solution of sodium chloride, dried over MgSO$_4$ and concentrated to dryness under vacuum. Purification on silica gel (800 g of silica gel, eluant: hexane/ethyl acetate 3:1) gives 22.4 g of 3-chloro-4-(ocetan-3-oxycarbonyl)-1-methyl-5-isopropylthiopyrazole in the form of an oil.

EXAMPLE 9

Preparation of 3-chloro-4-(oxetan-3-oxycarbonyl)-1-methylpyrazol-5-yl sulfochloride

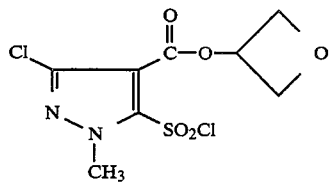

4.54 g of Cl$_2$ are introduced into a suspension of 5.8 g of 3-chloro-4-(oxetan-3-oxycarbonyl)-1-methyl-5-isopropylthiopyrazole and 5.75 g of sodium acetate in a mixture of 30 ml of glacial acetic acid and 30 ml of water at a temperature of −15° to −20° C. When the addition is complete, the reaction mixture is slowly warmed to room temperature and 70 ml of methylene chloride and 30 ml of an ice-water mixture are added. After phase separation, the aqueous phase is extracted with 100 ml of methylene chloride and the combined organic phase is washed with 50 ml of water and 50 ml of a saturated solution of sodium chloride, dried over MgSO$_4$ and concentrated to dryness under vacuum. Yield: 6.26 g of 3-chloro-4-(oxetan-3-oxycarbonyl)-1-methylpyrazol-5-yl sulfochloride in the form of a yellow oil.

EXAMPLE 10
Preparation of 3-chloro-4-(oxetan-3-oxycarbonyl)-1-methylpyrazol-5-yl sulfonamide (compound 6.001)

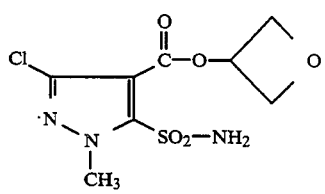

(6.001)

6.26 g of 3-chloro-4-(oxetan-3-oxycarbonyl)-1-methylpyrazol-5-yl sulfochloride are dissolved in 50 ml of THF and 1.1 g of $NH_3$ gas are introduced at a temperature of $-25°$ C. When the addition is complete, the reaction mixture is slowly warmed to room temperature, the suspension is filtered and the mother liquor is concentrated to dryness under vacuum. The residual viscous oil is purified on silica gel (150 g of silica gel, eluant: hexane/ethyl acetate 1.2:1). Yield: 2.1 g of 3-chloro-4-(oxetan-3-oxycarbonyl)-1-methylpyrazol-5-yl sulfonamide (compound 6.001) in the form of colourless crystals with a melting point 145°-147° C.

EXAMPLE 11
Preparation of N-[(3-oxetan-3-oxycarbonyl)-pyridin-2-yl sulfonyl]-N'-(4,6-dimethoxypyrimidin-2-yl)urea (compound 1.001)

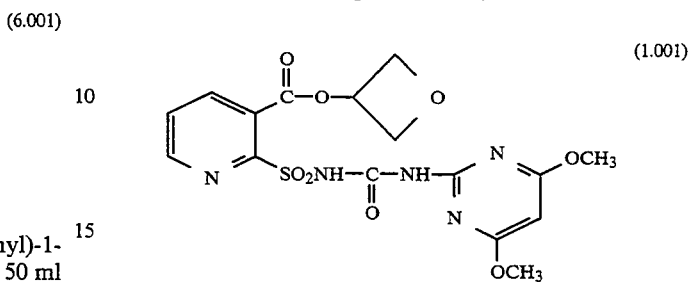

(1.001)

A mixture of 0.8 g of diazabicyclo[5.4.0]undec-7-ene and 5 ml of absolute of acetonitrile is added dropwise to a mixture of 1.36 g of 3-(oxetan-3-oxycarbonyl)pyridin-2-yl sulfonamide, 1.65 g of 4,6-dimethoxy-1,3-pyrimidinylphenylcarbamate and 10 ml of absolute acetonitrile at a temperature of 10° to 15° C. and the mixture is then stirred at room temperature for 2 hours. By pouring the reaction mixture into water and adding 10% hydrochloric acid dropwise until the pH is 5, 1.54 g of N-[(3-oxetan-3-oxycarbonyl)pyridin-2-ylsulfonyl]-N'-(4,6-dimethoxypyrimidin-2-yl)urea (compound 1.001) crystallise with a melting point of 175°-176° C.

TABLE 1

Compounds of formula Ia

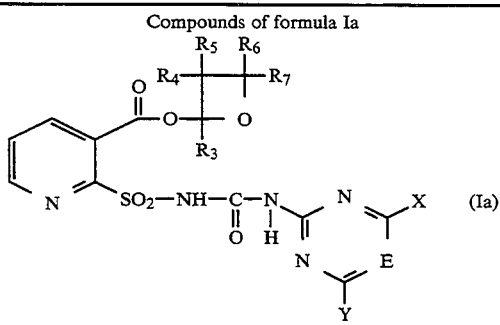

(Ia)

| Compound | $R_3$ | $R_4$ | $R_5$ | $R_6$ | $R_7$ | X | Y | E | mp [°C.] |
|---|---|---|---|---|---|---|---|---|---|
| 1.001 | H | H | H | H | H | $OCH_3$ | $OCH_3$ | CH | 175-176 |
| 1.002 | H | H | H | H | H | $OCH_3$ | $CH_3$ | N | 157-158 |
| 1.003 | H | H | H | H | H | $OCH_3$ | $OCH_3$ | N | |
| 1.004 | H | H | H | H | H | $OCH_3$ | $CH_3$ | CH | 140-142 |
| 1.005 | H | H | H | H | H | $CH_3$ | $CH_3$ | CH | 145-147 |
| 1.006 | H | H | H | H | H | $OCH_3$ | Cl | CH | |
| 1.007 | H | H | H | H | H | $OCH_3$ | $OCHF_3$ | CH | |
| 1.008 | H | H | H | H | H | $OCH_3$ | cyclopropyl | N | |
| 1.009 | H | H | H | H | H | $OCH_2CF_3$ | $N(CH_3)_2$ | N | |
| 1.010 | $CH_3$ | H | H | H | H | $OCH_3$ | $OCH_3$ | CH | |
| 1.011 | $CH_3$ | H | H | H | H | $OCH_3$ | $CH_3$ | N | |
| 1.012 | $CH_3$ | H | H | H | H | $OCH_3$ | $OCH_3$ | N | |
| 1.013 | $CH_3$ | H | H | H | H | $OCH_3$ | $CH_3$ | CH | |
| 1.014 | $CH_3$ | H | H | H | H | $CH_3$ | $CH_3$ | CH | |
| 1.015 | $CH_3$ | H | H | H | H | $OCH_3$ | Cl | CH | |
| 1.016 | $CH_3$ | H | H | H | H | $OCH_3$ | $OCHF_2$ | CH | |
| 1.017 | $CH_3$ | H | H | H | H | $OCH_2CF_3$ | $N(CH_3)_2$ | N | |
| 1.018 | $CH_3$ | H | H | H | H | $OCH_3$ | cyclopropyl | N | |
| 1.019 | H | $CH_3$ | H | H | H | $OCH_3$ | $OCH_3$ | CH | |
| 1.020 | H | $CH_3$ | H | H | H | $OCH_3$ | $CH_3$ | N | |

TABLE 1-continued

Compounds of formula Ia

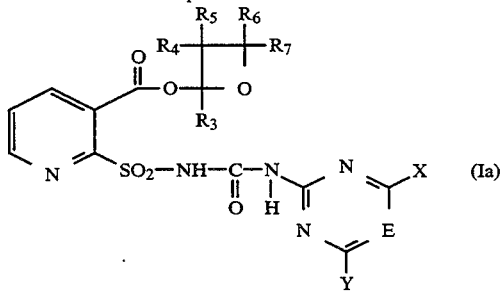

| Compound | $R_3$ | $R_4$ | $R_5$ | $R_6$ | $R_7$ | X | Y | E | mp [°C.] |
|---|---|---|---|---|---|---|---|---|---|
| 1.021 | H | $CH_3$ | H | H | H | $OCH_3$ | $OCH_3$ | N | |
| 1.022 | H | $CH_3$ | H | H | H | $OCH_3$ | $CH_3$ | CH | |
| 1.023 | H | $CH_3$ | H | H | H | $CH_3$ | $CH_3$ | CH | |
| 1.024 | H | $CH_3$ | H | H | H | $OCH_3$ | Cl | CH | |
| 1.025 | H | $CH_3$ | H | H | H | $OCH_3$ | $OCHF_2$ | CH | |
| 1.026 | H | $CH_3$ | H | H | H | $OCH_3$ | ▷ | N | |
| 1.027 | H | $CH_3$ | H | H | H | $OCH_2CF_3$ | $N(CH_3)_2$ | N | |
| 1.028 | H | $CH_3$ | $CH_3$ | H | H | $OCH_3$ | $OCH_3$ | CH | |
| 1.029 | H | $CH_3$ | $CH_3$ | H | H | $OCH_3$ | $CH_3$ | N | |
| 1.030 | H | $CH_3$ | $CH_3$ | H | H | $OCH_3$ | $OCH_3$ | N | |
| 1.031 | H | $CH_3$ | $CH_3$ | H | H | $OHC_3$ | $CH_3$ | CH | |
| 1.032 | H | $CH_3$ | $CH_3$ | H | H | $CH_3$ | $CH_3$ | CH | |
| 1.033 | H | $CH_3$ | $CH_3$ | H | H | $OCH_3$ | Cl | CH | |
| 1.034 | H | $CH_3$ | $CH_3$ | H | H | $OCH_3$ | $OCHF_2$ | CH | |
| 1.035 | H | $CH_3$ | $CH_3$ | H | H | $OCH_2CF_3$ | $N(CH_3)_2$ | N | |
| 1.036 | H | $CH_3$ | $CH_3$ | H | H | $OCH_3$ | ▷ | N | |
| 1.037 | H | $CH_3$ | $CH_3$ | $CH_3$ | H | $OCH_3$ | $OCH_3$ | CH | |
| 1.038 | H | $CH_3$ | $CH_3$ | $CH_3$ | H | $OCH_3$ | $CH_3$ | N | |
| 1.039 | H | $CH_3$ | $CH_3$ | $CH_3$ | H | $OCH_3$ | $OCH_3$ | N | |
| 1.040 | H | $CH_3$ | $CH_3$ | $CH_3$ | H | $OCH_3$ | $CH_3$ | CH | |
| 1.041 | H | $CH_3$ | $CH_3$ | $CH_3$ | H | $CH_3$ | $CH_3$ | CH | |
| 1.042 | H | $CH_3$ | $CH_3$ | $CH_3$ | H | $OCH_3$ | Cl | CH | |
| 1.043 | H | $CH_3$ | $CH_3$ | $CH_3$ | H | $OCH_3$ | $OCHF_2$ | CH | |
| 1.044 | H | $CH_3$ | $CH_3$ | $CH_3$ | H | $OCH_2CF_3$ | $N(CH_3)_2$ | N | |
| 1.045 | H | $CH_3$ | $CH_3$ | $CH_3$ | H | $OCH_3$ | ▷ | N | |
| 1.046 | H | $CH_3$ | $CH_3$ | $CH_3$ | $CH_3$ | $OCH_3$ | $OCH_3$ | CH | |
| 1.047 | H | $CH_3$ | $CH_3$ | $CH_3$ | $CH_3$ | $OCH_3$ | $CH_3$ | N | |
| 1.048 | H | $CH_3$ | $CH_3$ | $CH_3$ | $CH_3$ | $OCH_3$ | $OCH_3$ | N | |
| 1.049 | H | $CH_3$ | $CH_3$ | $CH_3$ | $CH_3$ | $OCH_3$ | $CH_3$ | CH | |
| 1.050 | H | $CH_3$ | $CH_3$ | $CH_3$ | $CH_3$ | $CH_3$ | $CH_3$ | CH | |
| 1.051 | H | $CH_3$ | $CH_3$ | $CH_3$ | $CH_3$ | $OCH_3$ | Cl | CH | |
| 1.052 | H | $CH_3$ | $CH_3$ | $CH_3$ | $CH_3$ | $OCH_3$ | $OCHF_2$ | CH | |
| 1.053 | H | $CH_3$ | $CH_3$ | $CH_3$ | $CH_3$ | $OCH_2CF_3$ | $N(CH_3)_2$ | N | |
| 1.054 | H | $CH_3$ | $CH_3$ | $CH_3$ | $CH_3$ | $OCH_3$ | ▷ | N | |
| 1.055 | $CH_3$ | $CH_3$ | $CH_3$ | $CH_3$ | $CH_3$ | $OCH_3$ | $OCH_3$ | CH | |
| 1.056 | $CH_3$ | $CH_3$ | $CH_3$ | $CH_3$ | $CH_3$ | $OCH_3$ | $CH_3$ | N | |
| 1.057 | $CH_3$ | $CH_3$ | $CH_3$ | $CH_3$ | $CH_3$ | $OCH_3$ | $OCH_3$ | N | |
| 1.058 | $CH_3$ | $CH_3$ | $CH_3$ | $CH_3$ | $CH_3$ | $OCH_3$ | $CH_3$ | CH | |
| 1.059 | $CH_3$ | $CH_3$ | $CH_3$ | $CH_3$ | $CH_3$ | $CH_3$ | $CH_3$ | CH | |
| 1.060 | $CH_3$ | $CH_3$ | $CH_3$ | $CH_3$ | $CH_3$ | $OCH_3$ | Cl | CH | |
| 1.061 | $CH_3$ | $CH_3$ | $CH_3$ | $CH_3$ | $CH_3$ | $OCH_3$ | $OCHF_2$ | CH | |
| 1.062 | $CH_3$ | $CH_3$ | $CH_3$ | $CH_3$ | $CH_3$ | $OCH_2CF_3$ | $N(CH_3)_2$ | N | |
| 1.063 | $CH_3$ | $CH_3$ | $CH_3$ | $CH_3$ | $CH_3$ | $OCH_3$ | ▷ | N | |

TABLE 2

Compounds of formula Ib

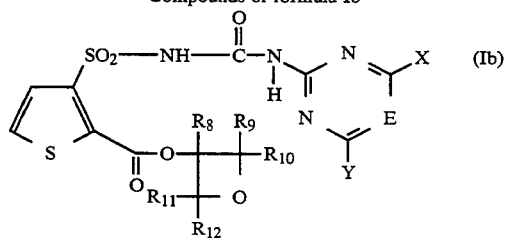

| Compound | R8 | R9 | R10 | R11 | R12 | X | Y | E | mp [°C.] |
|---|---|---|---|---|---|---|---|---|---|
| 2.001 | H | H | H | H | H | OCH3 | OCH3 | CH | 168–170 (decomp.) |
| 2.002 | H | H | H | H | H | OCH3 | CH3 | N | 126–128 |
| 2.003 | H | H | H | H | H | OCH3 | OCH3 | N | |
| 2.004 | H | H | H | H | H | CH3 | CH3 | CH | 183–185 |
| 2.005 | H | H | H | H | H | OCH3 | Cl | CH | |
| 2.006 | H | H | H | H | H | OCH3 | OCHF2 | CH | |
| 2.007 | H | H | H | H | H | OCH3 | ◁ | N | |
| 2.008 | CH3 | H | H | H | H | OCH3 | OCH3 | CH | |
| 2.009 | CH3 | H | H | H | H | OCH3 | CH3 | N | |
| 2.010 | CH3 | H | H | H | H | OCH3 | OCH3 | N | |
| 2.011 | CH3 | H | H | H | H | CH3 | CH3 | CH | |
| 2.012 | CH3 | H | H | H | H | OCH3 | Cl | CH | |
| 2.013 | CH3 | H | H | H | H | OCH3 | OCHF2 | CH | |
| 2.014 | CH3 | H | H | H | H | OCH3 | ◁ | N | |
| 2.015 | H | CH3 | H | H | H | OCH3 | OCH3 | CH | |
| 2.016 | H | CH3 | H | H | H | OCH3 | CH3 | N | |
| 2.017 | H | CH3 | H | H | H | OCH3 | OCH3 | N | |
| 2.018 | H | CH3 | H | H | H | CH3 | CH3 | CH | |
| 2.019 | H | CH3 | H | H | H | OCH3 | Cl | CH | |
| 2.020 | H | CH3 | H | H | H | OCH3 | OCHF2 | CH | |
| 2.021 | H | CH3 | H | H | H | OCH3 | ◁ | N | |
| 2.022 | H | CH3 | CH3 | H | H | OCH3 | OCH3 | CH | |
| 2.023 | H | CH3 | CH3 | H | H | OCH3 | CH3 | N | |
| 2.024 | H | CH3 | CH3 | H | H | OCH3 | OCH3 | N | |
| 2.025 | H | CH3 | CH3 | H | H | CH3 | CH3 | CH | |
| 2.026 | H | CH3 | CH3 | H | H | OCH3 | Cl | CH | |
| 2.027 | H | CH3 | CH3 | H | H | OCH3 | OCHF2 | CH | |
| 2.028 | H | CH3 | CH3 | H | H | OCH3 | ◁ | N | |
| 2.029 | H | CH3 | CH3 | CH3 | H | OCH3 | OCH3 | CH | |
| 2.030 | H | CH3 | CH3 | CH3 | H | OCH3 | CH3 | N | |
| 2.031 | H | CH3 | CH3 | CH3 | H | OCH3 | OCH3 | N | |
| 2.032 | H | CH3 | CH3 | CH3 | H | CH3 | CH3 | CH | |
| 2.033 | H | CH3 | CH3 | CH3 | H | OCH3 | Cl | CH | |
| 2.034 | H | CH3 | CH3 | CH3 | H | OCH3 | OCHF2 | CH | |
| 2.035 | H | CH3 | CH3 | CH3 | H | OCH3 | ◁ | N | |
| 2.036 | H | CH3 | CH3 | CH3 | CH3 | OCH3 | OCH3 | CH | |
| 2.037 | H | CH3 | CH3 | CH3 | CH3 | OCH3 | CH3 | N | |
| 2.038 | H | CH3 | CH3 | CH3 | CH3 | OCH3 | OCH3 | N | |
| 2.039 | H | CH3 | CH3 | CH3 | CH3 | CH3 | CH3 | CH | |
| 2.040 | H | CH3 | CH3 | CH3 | CH3 | OCH3 | Cl | CH | |
| 2.041 | H | CH3 | CH3 | CH3 | CH3 | OCH3 | OCHF2 | CH | |
| 2.042 | H | CH3 | CH3 | CH3 | CH3 | OCH3 | ◁ | N | |
| 2.043 | CH3 | CH3 | CH3 | CH3 | CH3 | OCH3 | OCH3 | CH | |

TABLE 2-continued

Compounds of formula Ib

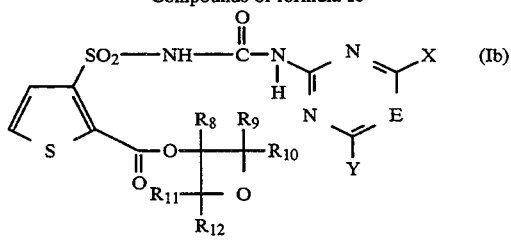

| Compound | $R_8$ | $R_9$ | $R_{10}$ | $R_{11}$ | $R_{12}$ | X | Y | E | mp [°C.] |
|---|---|---|---|---|---|---|---|---|---|
| 2.044 | $CH_3$ | $CH_3$ | $CH_3$ | $CH_3$ | $CH_3$ | $OCH_3$ | $CH_3$ | N | |
| 2.045 | $CH_3$ | $CH_3$ | $CH_3$ | $CH_3$ | $CH_3$ | $OCH_3$ | $OCH_3$ | N | |
| 2.046 | $CH_3$ | $CH_3$ | $CH_3$ | $CH_3$ | $CH_3$ | $CH_3$ | $CH_3$ | CH | |
| 2.047 | $CH_3$ | $CH_3$ | $CH_3$ | $CH_3$ | $CH_3$ | $OCH_3$ | Cl | CH | |
| 2.048 | $CH_3$ | $CH_3$ | $CH_3$ | $CH_3$ | $CH_3$ | $OCH_3$ | $CCHF_2$ | CH | |
| 2.049 | $CH_3$ | $CH_3$ | $CH_3$ | $CH_3$ | $CH_3$ | $OCH_3$ | ◁ | N | |

TABLE 3

Compound of formula Ic

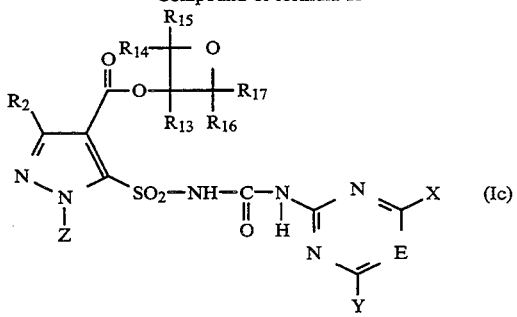

| Comp. | Z | $R_2$ | $R_{13}$ | $R_{14}$ | $R_{15}$ | $R_{16}$ | $R_{17}$ | X | Y | E | mp [°C.] |
|---|---|---|---|---|---|---|---|---|---|---|---|
| 3.001 | $CH_3$ | H | H | H | H | H | H | $OCH_3$ | $OCH_3$ | CH | 170–171 |
| 3.002 | $CH_3$ | H | H | H | H | H | H | $OCH_3$ | $CH_3$ | N | |
| 3.003 | $CH_3$ | H | H | H | H | H | H | $OCH_3$ | $OCH_3$ | N | |
| 3.004 | $CH_3$ | H | H | H | H | H | H | $CH_3$ | $CH_3$ | CH | |
| 3.005 | $CH_3$ | H | H | H | H | H | H | $OCH_3$ | Cl | CH | |
| 3.006 | $CH_3$ | H | H | H | H | H | H | $OCH_3$ | $OCHF_2$ | CH | |
| 3.007 | $CH_3$ | H | H | H | H | H | H | $OCH_3$ | ◁ | N | |
| 3.008 | $CH_3$ | Cl | H | H | H | H | H | $OCH_3$ | $OCH_3$ | CH | |
| 3.009 | $CH_3$ | Cl | H | H | H | H | H | $OCH_3$ | $CH_3$ | N | |
| 3.010 | $CH_3$ | Cl | H | H | H | H | H | $OCH_3$ | $OCH_3$ | N | |
| 3.011 | $CH_3$ | Cl | H | H | H | H | H | $CH_3$ | $CH_3$ | CH | 169–170 |
| 3.012 | $CH_3$ | Cl | H | H | H | H | H | $OCH_3$ | Cl | CH | |
| 3.013 | $CH_3$ | Cl | H | H | H | H | H | $OCH_3$ | $OCHF_2$ | CH | |
| 3.014 | $CH_3$ | Cl | H | H | H | H | H | $OCH_3$ | ◁ | N | |
| 3.015 | $CH_3$ | H | H | $CH_3$ | H | H | H | $OCH_3$ | $OCH_3$ | CH | |
| 3.016 | $CH_3$ | H | H | $CH_3$ | H | H | H | $OCH_3$ | $CH_3$ | N | |
| 3.017 | $CH_3$ | H | H | $CH_3$ | H | H | H | $OCH_3$ | $OCH_3$ | N | |
| 3.018 | $CH_3$ | H | H | $CH_3$ | H | H | H | $CH_3$ | $CH_3$ | H | |
| 3.019 | $CH_3$ | H | H | $CH_3$ | H | H | H | $OCH_3$ | Cl | CH | |
| 3.020 | $CH_3$ | H | H | $CH_3$ | H | H | H | $OCH_3$ | $OCHF_2$ | CH | |
| 3.021 | $CH_3$ | H | H | $CH_3$ | H | H | H | $OCH_3$ | ◁ | N | |
| 3.022 | $CH_3$ | Cl | H | $CH_3$ | H | H | H | $OCH_3$ | $OCH_3$ | CH | |
| 3.023 | $CH_3$ | Cl | H | $CH_3$ | H | H | H | $OCH_3$ | $CH_3$ | N | |
| 3.024 | $CH_3$ | Cl | H | $CH_3$ | H | H | H | $OCH_3$ | $OCH_3$ | N | |
| 3.025 | $CH_3$ | Cl | H | $CH_3$ | H | H | H | $CH_3$ | $CH_3$ | CH | |
| 3.026 | $CH_3$ | Cl | H | $CH_3$ | H | H | H | $OCH_3$ | Cl | CH | |

TABLE 3-continued

Compound of formula Ic

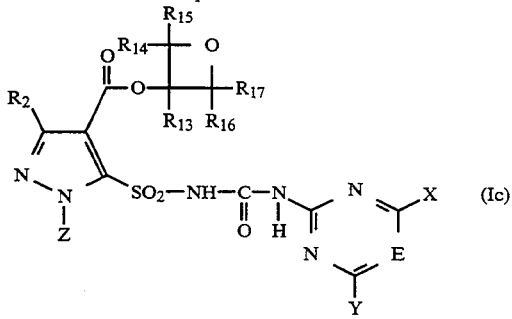

| Comp. | Z | R₂ | R₁₃ | R₁₄ | R₁₅ | R₁₆ | R₁₇ | X | Y | E | mp [°C.] |
|---|---|---|---|---|---|---|---|---|---|---|---|
| 3.027 | CH₃ | Cl | CH₃ | H | H | H | H | OCH₃ | OCHF₂ | CH | |
| 3.028 | CH₃ | Cl | CH₃ | H | H | H | H | OCH₃ | ◁ | N | |
| 3.029 | CH₃ | H | H | CH₃ | H | H | H | OCH₃ | OCH₃ | CH | |
| 3.030 | CH₃ | H | H | CH₃ | H | H | H | OCH₃ | CH₃ | N | |
| 3.031 | CH₃ | H | H | CH₃ | H | H | H | OCH₃ | OCH₃ | N | |
| 3.032 | CH₃ | H | H | CH₃ | H | H | H | CH₃ | CH₃ | CH | |
| 3.033 | CH₃ | H | H | CH₃ | H | H | H | OCH₃ | Cl | CH | |
| 3.034 | CH₃ | H | H | CH₃ | H | H | H | OCH₃ | OCHF₂ | CH | |
| 3.035 | CH₃ | H | H | CH₃ | H | H | H | OCH₃ | ◁ | N | |
| 3.036 | CH₃ | Cl | H | CH₃ | H | H | H | OCH₃ | OCH₃ | CH | |
| 3.037 | CH₃ | Cl | H | CH₃ | H | H | H | OCH₃ | CH₃ | N | |
| 3.038 | CH₃ | Cl | H | CH₃ | H | H | H | OCH₃ | OCH₃ | N | |
| 3.039 | CH₃ | Cl | H | CH₃ | H | H | H | CH₃ | CH₃ | CH | |
| 3.040 | CH₃ | Cl | H | CH₃ | H | H | H | OCH₃ | Cl | CH | |
| 3.041 | CH₃ | Cl | H | CH₃ | H | H | H | OCH₃ | CCHF₂ | CH | |
| 3.042 | CH₃ | Cl | H | CH₃ | H | H | H | OCH₃ | ◁ | N | |
| 3.043 | 2-pyr. | H | H | H | H | H | H | OCH₃ | OCH₃ | CH | 165–166 |
| 3.044 | 2-pyr. | H | H | H | H | H | H | OCH₃ | CH₃ | N | 159–162 |
| 3.045 | 2-pyr. | H | H | H | H | H | H | OCH₃ | OCH₃ | N | |
| 3.046 | 2-pyr. | H | H | H | H | H | H | CH₃ | CH₃ | CH | 177–179 |
| 3.047 | 2-pyr. | H | H | H | H | H | H | OCH₃ | Cl | CH | |
| 3.048 | 2-pyr. | H | H | H | H | H | H | OCH₃ | OCHF₂ | CH | |
| 3.049 | 2-pyr. | H | H | H | H | H | H | OCH₃ | ◁ | N | |
| 3.050 | 2-pyr. | H | H | H | H | H | H | OCH₃ | CH₃ | CH | 169–170 |
| 3.051 | 2-pyr. | Cl | H | H | H | H | H | OCH₃ | OCH₃ | CH | |
| 3.052 | 2-pyr. | Cl | H | H | H | H | H | OCH₃ | CH₃ | N | |
| 3.053 | 2-pyr. | Cl | H | H | H | H | H | OCH₃ | OCH₃ | N | |
| 3.054 | 2-pyr. | Cl | H | H | H | H | H | CH₃ | CH₃ | CH | |
| 3.055 | 2-pyr. | Cl | H | H | H | H | H | OCH₃ | Cl | CH | |
| 3.056 | 2-pyr. | Cl | H | H | H | H | H | OCH₃ | OCHF₂ | CH | |
| 3.057 | 2-pyr. | Cl | H | H | H | H | H | OCH₃ | ◁ | N | |
| 3.058 | 2-pyr. | H | CH₃ | H | H | H | H | OCH₃ | OCH₃ | CH | |
| 3.059 | 2-pyr. | H | CH₃ | H | H | H | H | OCH₃ | CH₃ | N | |
| 3.060 | 2-pyr. | H | CH₃ | H | H | H | H | OCH₃ | OCH₃ | N | |
| 3.061 | 2-pyr. | H | CH₃ | H | H | H | H | CH₃ | CH₃ | CH | |
| 3.062 | 2-pyr. | H | CH₃ | H | H | H | H | OCH₃ | Cl | CH | |
| 3.063 | 2-pyr. | H | CH₃ | H | H | H | H | OCH₃ | OCHF₂ | CH | |
| 3.064 | 2-pyr. | H | CH₃ | H | H | H | H | OCH₃ | ◁ | N | |
| 3.065 | 2-pyr. | Cl | CH₃ | H | H | H | H | OCH₃ | OCH₃ | CH | |
| 3.066 | 2-pyr. | Cl | CH₃ | H | H | H | H | OCH₃ | CH₃ | N | |

TABLE 3-continued

Compound of formula Ic

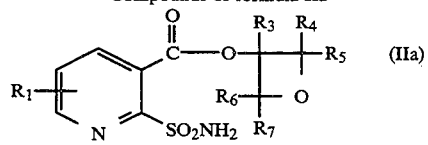

(Ic)

| Comp. | Z | R2 | R13 | R14 | R15 | R16 | R17 | X | Y | E | mp [°C.] |
|---|---|---|---|---|---|---|---|---|---|---|---|
| 3.067 | 2-pyr. | Cl | CH3 | H | H | H | H | OCH3 | OCH3 | N | |
| 3.068 | 2-pyr. | Cl | CH3 | H | H | H | H | CH3 | CH3 | CH | |
| 3.069 | 2-pyr. | Cl | CH3 | H | H | H | H | OCH3 | Cl | CH | |
| 3.070 | 2-pyr. | Cl | CH3 | H | H | H | H | OCH3 | OCHF2 | CH | |
| 3.071 | 2-pyr. | H | CH3 | CH3 | H | H | H | OCH3 | ◁ | N | |
| 3.072 | 2-pyr. | H | CH3 | CH3 | H | H | H | OCH3 | OCH3 | CH | |
| 3.073 | 2-pyr. | H | CH3 | CH3 | H | H | H | OCH3 | CH3 | N | |
| 3.074 | 2-pyr. | H | CH3 | CH3 | H | H | H | OCH3 | OCH3 | N | |
| 3.075 | 2-pyr. | H | CH3 | CH3 | H | H | H | CH3 | CH3 | CH | |
| 3.076 | 2-pyr. | H | CH3 | CH3 | H | H | H | OCH3 | Cl | CH | |
| 3.077 | 2-pyr. | H | CH3 | CH3 | H | H | H | OCH3 | OCHF2 | CH | |
| 3.078 | 2-pyr. | H | CH3 | CH3 | H | H | H | OCH3 | ◁ | N | |
| 3.079 | 2-pyr. | Cl | CH3 | CH3 | H | H | H | OCH3 | OCH3 | CH | |
| 3.080 | 2-pyr. | Cl | CH3 | CH3 | H | H | H | OCH3 | CH3 | N | |
| 3.081 | 2-pyr. | Cl | CH3 | CH3 | H | H | H | OCH3 | OCH3 | N | |
| 3.082 | 2-pyr. | Cl | CH3 | CH3 | H | H | H | CH3 | CH3 | CH | |
| 3.083 | 2-pyr. | Cl | CH3 | CH3 | H | H | H | OCH3 | Cl | CH | |
| 3.084 | 2-pyr. | Cl | CH3 | CH3 | H | H | H | OCH3 | OCHF2 | CH | |
| 3.085 | 2-pyr. | Cl | CH3 | CH3 | H | H | H | OCH3 | ◁ | N | |

TABLE 4

Compounds of formula IIa

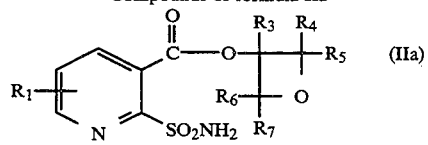

(IIa)

| Compound | R1 | R3 | R4 | R5 | R6 | R7 | mp [°C.] |
|---|---|---|---|---|---|---|---|
| 4.001 | H | H | H | H | H | H | 142–144 |
| 4.002 | H | CH3 | H | H | H | H | |
| 4.003 | H | H | CH3 | H | H | H | |
| 4.004 | H | CH3 | CH3 | H | H | H | |
| 4.005 | H | H | CH3 | CH3 | CH3 | H | |
| 4.006 | H | H | CH3 | CH3 | CH3 | CH3 | |
| 4.007 | H | CH3 | CH3 | CH3 | CH3 | CH3 | |

TABLE 5

Compounds of formula IIb

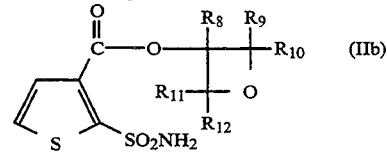

(IIb)

| Compound | R8 | R9 | R10 | R11 | R12 | mp [°C.] |
|---|---|---|---|---|---|---|
| 5.001 | H | H | H | H | H | 158–160 |
| 5.002 | CH3 | H | H | H | H | |
| 5.003 | H | CH3 | H | H | H | |
| 5.004 | H | CH3 | CH3 | H | H | |
| 5.005 | H | CH3 | CH3 | CH3 | H | |
| 5.006 | H | CH3 | CH3 | CH3 | CH3 | |
| 5.007 | CH3 | CH3 | CH3 | CH3 | CH3 | |

TABLE 6

Compounds of formula IIc $$\text{(IIc)}$$

with structure showing $R_2$, $R_{13}$, $R_{14}$, $R_{15}$, $R_{16}$, $R_{17}$, N-N-Z, $SO_2NH_2$, and C(=O)-O- linkage.

| Compound | Z | $R_2$ | $R_{13}$ | $R_{14}$ | $R_{15}$ | $R_{16}$ | $R_{17}$ | mp [°C] |
|---|---|---|---|---|---|---|---|---|
| 6.001 | $CH_3$ | H | H | H | H | H | H | 145–147 |
| 6.002 | $CH_3$ | Cl | H | H | H | H | H | |
| 6.003 | $CH_3$ | H | $CH_3$ | H | H | H | H | |
| 6.004 | $CH_3$ | H | H | $CH_3$ | H | H | H | |
| 6.005 | $CH_3$ | H | H | $CH_3$ | $CH_3$ | H | H | |
| 6.006 | $CH_3$ | H | H | $CH_3$ | $CH_3$ | $CH_3$ | H | |
| 6.007 | $CH_3$ | H | H | $CH_3$ | $CH_3$ | $CH_3$ | $CH_3$ | |
| 6.008 | $CH_3$ | H | $CH_3$ | $CH_3$ | $CH_3$ | $CH_3$ | $CH_3$ | |
| 6.009 | $CH_3$ | H | H | H | H | H | $C_2H_5$ | |
| 6.010 | $CH_3$ | Cl | $CH_3$ | H | H | H | H | |
| 6.011 | $CH_3$ | Cl | H | $CH_3$ | H | H | H | |
| 6.012 | $CH_3$ | Cl | H | $CH_3$ | $CH_3$ | H | H | |
| 6.013 | $CH_3$ | Cl | H | $CH_3$ | $CH_3$ | $CH_3$ | H | |
| 6.014 | $CH_3$ | Cl | H | $CH_3$ | $CH_3$ | $CH_3$ | $CH_3$ | |
| 6.015 | $CH_3$ | Cl | $CH_3$ | $CH_3$ | $CH_3$ | $CH_3$ | $CH_3$ | |
| 6.016 | 2-pyr. | H | H | H | H | H | H | |
| 6.017 | 2-pyr. | Cl | H | H | H | H | H | |
| 6.018 | 2-pyr. | H | $CH_3$ | H | H | H | H | |
| 6.019 | 2-pyr. | H | H | $CH_3$ | H | H | H | |
| 6.020 | 2-pyr. | H | H | $CH_3$ | $CH_3$ | H | H | |
| 6.021 | 2-pyr. | H | H | $CH_3$ | $CH_3$ | $CH_3$ | H | |
| 6.022 | 2-pyr. | H | H | $CH_3$ | $CH_3$ | $CH_3$ | $CH_3$ | |
| 6.023 | 2-pyr. | H | $CH_3$ | $CH_3$ | $CH_3$ | $CH_3$ | $CH_3$ | |
| 6.024 | 2-pyr. | Cl | $CH_3$ | H | H | H | H | |
| 6.025 | 2-pyr. | Cl | H | $CH_3$ | | H | H | |
| 6.026 | 2-pyr. | Cl | H | $CH_3$ | $CH_3$ | H | H | |
| 6.027 | 2-pyr. | Cl | H | $CH_3$ | $CH_3$ | $CH_3$ | H | |
| 6.028 | 2-pyr. | Cl | H | $CH_3$ | $CH_3$ | $CH_3$ | $CH_3$ | |
| 6.029 | 2-pyr. | Cl | $CH_3$ | $CH_3$ | $CH_3$ | $CH_3$ | $CH_3$ | |

| F1. Wettable powders | a) | b) | c) |
|---|---|---|---|
| Compound of Tables 1–3 | 20% | 50% | 0.5% |
| sodium ligninsulfonate | 5% | 5% | 5 |
| sodium laurylsulfate | 3% | — | —% |
| sodium diisobutylnaphthalene-sulfonate | — | 6% | 6% |
| octylphenol polyethylene glycol ether (7–8 mol EO) | — | 2% | 2 |
| highly dispersed silica gel | 5% | 27% | 27% |
| kaolin | 67% | —% | — |
| sodium chloride | — | — | 59.5% |

The active ingredient is throughly mixed with the adjuvants and the mixture is ground in a suitable mill to give wettable powders which can be diluted with water to form suspensions of each desired concentration.

| F2. Water-dispersible granulate | a) | b) |
|---|---|---|
| compound of Tables 1–3 | 75% | 5% |
| sodium dibutylnaphthalene-sulfonate | 2% | 0.5% |
| gum arabic | 1% | 1% |
| sodium sulfate | 5% | 3% |
| sodium ligninsulfonate | 17% | 15% |
| kaolin | — | 75.5% |

Emulsions of any desired concentration can be obtained by diluting such concentrates with water.

| F3. Dusts | a) | b) |
|---|---|---|
| compound of Tables 1–3 | 0.1% | 1% |
| talcum | 99.9% | — |
| kaolin | — | 99% |

Ready for use dusts are obtained by intimately mixing the carriers with the active ingredient.

| F4. Extruder granulate | a) | b) |
|---|---|---|
| compound of Tables 1–3 | 10% | 1% |
| sodium ligninsulfonate | 2% | 2% |
| carboxymethyl cellulose | 1% | 1% |
| kaolin | 87% | 96% |

The active ingredient is mixed with the adjuvants and the mixture is moistened with water. This mixture is extruded and then dried in a stream of air.

| F5. Coated granulate | |
|---|---|
| compound of Tables 1–3 | 3% |
| polyethylene glycol (MG200) | 3% |
| kaolin | 94% |

The finely ground active ingredient is uniformly applied in a mixer to the kaolin moistened with polyethylene glycol. Non-dusty coated granulates are obtained in this manner.

| F6. Suspension concentrate | a) | b) |
|---|---|---|
| compound of Tables 1–3 | 5% | 40% |
| ethylene glycol | 10% | 10% |
| nonylphenol polyethylene glycol ether (15 mol EO) | 1% | 6% |
| sodium ligninsulfonate | 5% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 77% | 32% |

The finely ground active ingredient is intimately mixed with the adjuvants to give a suspension concentrate from which suspensions of any desired concentration can be prepared by dilution with water.

| F7. Salt solution | |
|---|---|
| compound of Tables 1–3 | 5% |
| isopropylamine | 1% |
| octylphenol polyethylene glycol ether (78 mol EO) | 3% |
| water | 91% |

The compounds of formula I are used in unmodified form or preferably together with the adjuvants commonly employed in the art of formulation, and are therefore formulated in known manner to emulsifiable concentrates, directly sprayable or dilutable solutions. dilute emulsions, wettable powders, soluble powders, dusts, granulates, and also encapsulations in e.g. polymer substances. As with the compositions, the methods of application, e.g. spraying, atomising, dusting, scattering or pouring, are chosen in accordance with the intended objectives and the prevailing circumstances.

BIOLOGICAL EXAMPLES

Example B1: Preemergence herbicidal action

Plastic pots are filled with expanded vermiculite (density: 0.135 g/cm$^3$, water-adsorbing capacity: 0.565 l/l). After the non-adsorptive vermiculite has been saturated with an aqueous emulsion in deionised water which contains the test compound in a concentration of 70.8 ppm, seeds of the following plants are sown on the surface: Nasturtium officinalis, Agrostis tenuis, Stellaria media and Digitaria sanguinalis. The pots are then kept in a climatic chamber at 20° C., an illumination of about 20 lux and a relative humidity of 70%. During the germinating phase of 4 to 5 days, the pots are covered with light-permeable material and watered with deionised water to increase the local humidity. After the 5th day, 0.5% of a commercial liquid fertiliser is added to the water. The test is evaluated 12 days after sowing and the action on the plants is assessed in accordance with the following rating:

1: plants have not emerged or are totally withered
2-3: very pronounced action
4-6: medium action
7-8: weak action
9: no action (as untreated controls).

TABLE B1

Preemergence action
Concentration of the test compound emulsion: 70 ppm

| Test plant: Compound | Nasturtium | Stellaria | Agrostis | Digitaria |
|---|---|---|---|---|
| 1.001 | 2 | 2 | 2 | 2 |
| 1.002 | 2 | 2 | 3 | 3 |
| 1.004 | 5 | 4 | 3 | 4 |
| 1.005 | 3 | 3 | 3 | 3 |
| 2.001 | 2 | 2 | 1 | 2 |
| 2.002 | 2 | 2 | 4 | 2 |
| 2.004 | 3 | 2 | 2 | 2 |

Example B2: Postemergence herbicidal activity (contact herbicide)

A number of weeds, monocots as well as dicots, are sprayed postemergence (in the 4-6 leaf stage) with an aqueous dispersion of the test compound prepared according to Example F6 at a rate of application of 8-500 g a.i./ha. The plants are kept at 24°-26° C. and 45-60% relative humidity. The test is evaluated 15 days after treatment.

After 3 weeks the herbicidal activity is evaluated by means of a rating scheme on a scale of 1-9 (1= complete damage, 9= no activity) in comparison with an untreated control group. Ratings of 1 to 4 (especially 1 to 3) indicate good to very good herbicidal action. Ratings of 6 to 9 (especially from 7 to 9) indicate good tolerance (especially by cultivated plants).

In this test the compounds of formula I exhibit superior herbicidal action. The same results are obtained by formulating the compounds of formula I according to Examples F1 to F5 and F7.

What is claimed is:

1. A compound of formula I

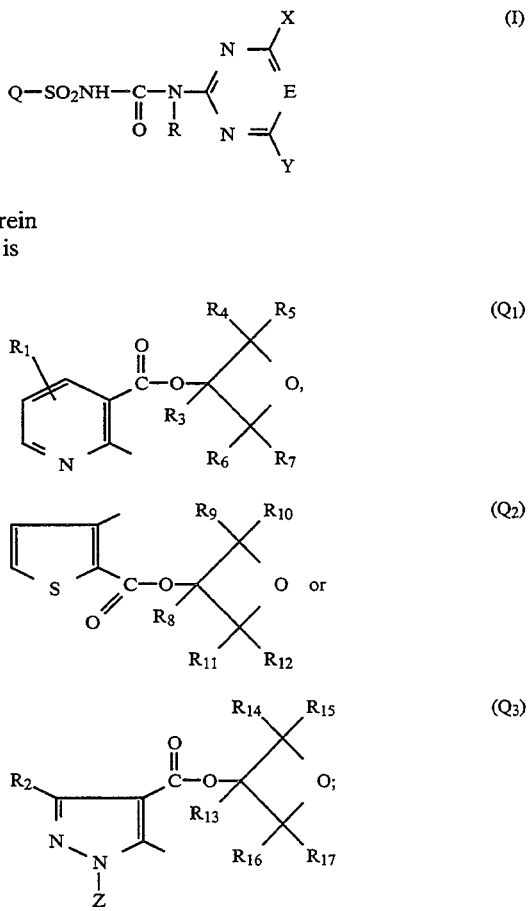

wherein Q is

R is hydrogen or methyl;
$R_1$ is hydrogen, fluoro, chloro, $C_1$-$C_4$alkyl or methoxy;
$R_2$ is hydrogen, fluoro or chloro;
$R_3$, $R_4$, $R_5$, $R_6$ and $R_7$ are each independently of one another hydrogen or $C_1$-$C_4$alkyl;
$R_8$, $R_9$, $R_{10}$, $R_{11}$ and $R_{12}$ are each independently of one another hydrogen or $C_1$-$C_4$alkyl;
$R_{13}$, $R_{14}$, $R_{15}$, $R_{16}$ and $R_{17}$ are each independently of one another hydrogen or $C_1$-$C_4$alkyl;
Z is methyl or 2-pyridyl;
E is methine
X is $C_1$-$C_4$alkyl, $C_1$-$C_4$alkoxy, $C_1$-$C_4$haloalkoxy, $C_1$-$C_4$haloalkylthio, $C_1$-$C_4$alkylthio, $C_2$-$C_5$alkoxyalkyl, $C_2$-$C_5$alkoxyalkoxy, $C_2$-$C_5$alkylthioalkyl or cyclopropyl;
Y is $C_1$-$C_4$alkyl, $C_1$-$C_4$alkoxy, $C_1$-$C_4$haloalkoxy, $C_1$-$C_4$haloalkyl, $C_1$-$C_4$haloalkylthio, $C_1$-$C_4$alkylthio, halogen, $C_2$-$C_5$alkoxyalkyl, $C_2$-$C_5$alkoxyalkoxy, amino, $C_1$-$C_3$alkylamino or di-($C_1$-$C_3$alkyl)amino;
or a salt thereof.

2. A compound of formula I according to claim 1, wherein R is hydrogen.

3. A compound of formula I according to claim 2, wherein Q is $Q_1$.

4. A compound of formula I according to claim 1, wherein Q is $Q_2$, X is $C_1$-$C_3$alkyl, $C_1$-$C_3$alkoxy, $C_1$-$C_2$haloalkoxy or cyclopropyl; and Y is $C_1$-$C_3$alkyl, $C_1$-$C_3$alkoxy, $C_1$-$C_2$haloalkoxy, trifluoromethyl, difluoromethyl, fluoromethyl, methoxymethyl, fluoro, chloro, amino, methylamino, dimethylamino, or methylthio.

5. A compound of formula I according to claim 2, wherein Q is Q$_3$.

6. A compound of formula I according to claim 3, wherein R$_1$ is hydrogen.

7. A compound of formula I according to claim 5, wherein R$_2$ is hydrogen or chloro.

8. A compound of formula I according to claim 3, wherein R$_3$, R$_4$, R$_5$, R$_6$ and R$_7$ are hydrogen.

9. A compound of formula I according to claim 4, wherein R$_8$, R$_9$, R$_{10}$, R$_{11}$ and R$_{12}$ are hydrogen.

10. A compound of formula I according to claim 5, wherein R$_{13}$, R$_{14}$, R$_{15}$, R$_{16}$ and R$_{17}$ are hydrogen.

11. A compound of formula I according to claim 1, wherein X is C$_1$-C$_3$alkyl, C$_1$-C$_3$alkoxy, C$_1$-C$_2$haloalkoxy or cyclopropyl, preferably methyl, methoxy, difluoromethoxy, ethoxy or cyclopropyl; and Y is C$_1$-C$_3$alkyl, C$_1$-C$_3$alkoxy, C$_1$-C$_2$haloalkoxy, trifluoromethyl, difluoromethyl, fluoromethyl, methoxymethyl, fluoro, chloro, amino, methylamino, dimethylamino or methylthio.

12. A compound of formula I according to claim 11, wherein X is methyl, ethyl, methoxy, difluormethoxy, ethoxy, 2,2,2-trifluoroethoxy, chloro, methylamino, dimethylamino or methoxymethyl.

13. N-[(3-oxetan-3-oxycarbonyl)-pyridin-2-yl-sulfonyl]-N'-(4,6-dimethoxypyrimidin-2-yl)urea of the formula

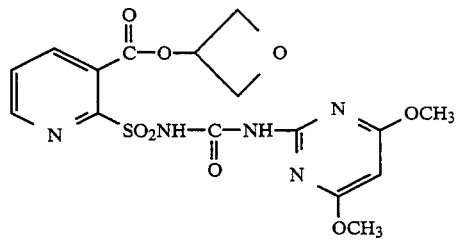

according to claim 1.

14. A herbicidal and plant growth regulating composition, which contains at least an effective amount of a sulfonylurea of formula I as claimed in claim 1 and an agrochemically acceptable carries.

15. A composition according to claim 14, which contains from 0.1 to 95% of said compound of formula I.

16. A method of controlling undesirable plant growth, which comprises applying a herbicidally effective amount of a compound of formula I as claimed in claim 1, or of a composition containing such a compound, to said plants or to the locus thereof.

17. A method according to claim 16, wherein the compound of formula I is applied in a concentration of 0.001 to 2 kg per hectare.

18. A method of inhibiting plant growth, which comprises applying a growth-inhibitingly effective amount of a compound of formula I as claimed in claim 1, or of a composition containing such a compound, to said plants or to the locus thereof.

19. A method according to claim 16 for the selective control of weeds pre- and postemergence in crops of useful plants.

* * * * *